(12) United States Patent
Hedrick et al.

(10) Patent No.: US 7,368,089 B2
(45) Date of Patent: May 6, 2008

(54) SYSTEMS AND METHODS FOR PRODUCING FLUOROCARBONS

(75) Inventors: Vicki E. Hedrick, Brookston, IN (US); Janet K. Boggs, Brownsburg, IN (US); Stephen M. Brandstadter, Indianapolis, IN (US); Mitchel Cohn, West Lafayette, IN (US)

(73) Assignee: Great Lakes Chemical Corporation, West Lafayette, IN (US)

( * ) Notice: Subject to any disclaimer, the term of this patent is extended or adjusted under 35 U.S.C. 154(b) by 121 days.

(21) Appl. No.: 11/069,180

(22) Filed: Feb. 28, 2005

(65) Prior Publication Data

US 2005/0148804 A1 Jul. 7, 2005

Related U.S. Application Data

(62) Division of application No. 10/641,527, filed on Aug. 13, 2003.

(51) Int. Cl.
*B01J 19/00* (2006.01)
(52) U.S. Cl. .................. 422/131; 422/190; 422/211
(58) Field of Classification Search ............... 422/211, 422/190, 131; 570/156, 158, 176
See application file for complete search history.

(56) References Cited

U.S. PATENT DOCUMENTS

| | | | |
|---|---|---|---|
| 1,132,636 A | 3/1915 | Taylor et al. | |
| 1,926,395 A | 9/1933 | Midgley, Jr. | |
| 1,926,396 A | 9/1933 | Midgley, Jr. | |
| 2,005,706 A | 6/1935 | Daudt et al. | |
| 2,005,707 A | 6/1935 | Daudt et al. | |
| 2,021,981 A | 11/1935 | Bichowsky | |
| 2,413,696 A | 1/1947 | Downing et al. | |
| 2,456,028 A | 12/1948 | Simons | |
| 2,494,064 A | 1/1950 | Simons et al. | |
| 2,519,983 A | 8/1950 | Simons | |
| 2,576,823 A | 11/1951 | Benning et al. | |
| 2,697,124 A | 12/1954 | Mantell et al. | |

(Continued)

FOREIGN PATENT DOCUMENTS

CA 902590 A 8/1962

(Continued)

OTHER PUBLICATIONS

*Scientific Assessment of Stratospheric Ozone: 1989* sponsored by the United Nations Environmental Program.

(Continued)

*Primary Examiner*—N. Bhat
(74) *Attorney, Agent, or Firm*—Wells St. John P.S.

(57) ABSTRACT

Systems and methods for producing fluorocarbons are provided that include contacting a saturated halogenated fluorocarbon with hydrogen and catalyst to produce a saturated hydrofluorocarbon and an unsaturated fluorocarbon. Aspects of the present invention describe systems and methods for contacting saturated halogenated fluorocarbons such as $CF_3CClFCF_3$ and/or $CF_3CCl_2CF_3$ with hydrogen and catalyst. Systems and methods of the present invention also describe contacting saturated halogenated fluorocarbons with catalysts having one or more of K, Zr, Na, Ni, Cu, Ni, Zn, Fe, Mn, Co, Ti, and Pd. Aspects of the present invention also describe contacting saturated halogenated fluorocarbons with hydrogen under pressure. Saturated hydroflourocarbons and unsaturated fluorocarbons produced in accordance with the systems and methods of the present invention can include one or more of $CF_3CFHCF_3$, $CF_3CH_2CF_3$, $CF_3CHClCF_3$, $CF_3CF=CF_2$, $CF_3CH=CF_2$, and $CF_3CCl=CF_2$.

10 Claims, 1 Drawing Sheet

U.S. PATENT DOCUMENTS

| | | |
|---|---|---|
| 2,900,423 A | 8/1959 | Smith et al. |
| 2,942,036 A | 6/1960 | Smith et al. |
| 3,080,430 A | 3/1963 | Cohen |
| 3,258,500 A | 6/1966 | Swamer et al. |
| 3,436,430 A | 4/1969 | Hall et al. |
| 3,479,286 A | 11/1969 | Gambaretto et al. |
| 3,636,173 A | 1/1972 | Gardner |
| 3,656,553 A | 4/1972 | Rainaldi et al. |
| 3,715,438 A | 2/1973 | Huggett |
| 3,803,241 A | 4/1974 | Stolkin et al. |
| 3,822,207 A | 7/1974 | Howard et al. |
| 3,844,354 A | 10/1974 | Larsen |
| 4,014,799 A | 3/1977 | Owens |
| 4,158,023 A | 6/1979 | von Halasz |
| 4,225,404 A | 9/1980 | Dietrich et al. |
| 4,226,728 A | 10/1980 | Kung |
| 4,446,923 A | 5/1984 | Martin |
| 4,459,213 A | 7/1984 | Uchida et al. |
| 4,536,298 A | 8/1985 | Kamei et al. |
| 4,668,407 A | 5/1987 | Gerard et al. |
| 4,810,403 A | 3/1989 | Bivens et al. |
| 4,826,610 A | 5/1989 | Thacker |
| 4,851,595 A | 7/1989 | Gumprecht |
| 4,876,405 A | 10/1989 | Gervasutti |
| 4,885,409 A | 12/1989 | Gardano et al. ............ 568/834 |
| 4,937,398 A | 6/1990 | Tung et al. |
| 4,945,119 A | 7/1990 | Smits et al. |
| 4,954,271 A | 9/1990 | Green |
| 4,996,374 A | 2/1991 | Lin et al. |
| 5,040,609 A | 8/1991 | Dougherty et al. |
| 5,043,491 A | 8/1991 | Webster et al. |
| 5,057,634 A | 10/1991 | Webster et al. |
| 5,068,472 A | 11/1991 | Webster et al. |
| 5,068,473 A | 11/1991 | Kellner et al. |
| 5,084,190 A | 1/1992 | Fernandez |
| 5,115,868 A | 5/1992 | Dougherty, Jr. et al. |
| 5,141,654 A | 8/1992 | Fernandez |
| 5,146,018 A | 9/1992 | Kellner et al. |
| 5,171,901 A | 12/1992 | Gassen et al. |
| 5,177,273 A | 1/1993 | Bruhnke et al. |
| 5,220,083 A | 6/1993 | Webster et al. |
| 5,268,343 A | 12/1993 | Hopp et al. |
| 5,302,765 A | 4/1994 | Manzer et al. .............. 570/123 |
| 5,364,992 A | 11/1994 | Manogue et al. |
| 5,416,246 A | 5/1995 | Krespan et al. |
| 5,430,204 A | 7/1995 | Manogue et al. |
| 5,446,219 A | 8/1995 | Manogue et al. |
| 5,510,545 A | 4/1996 | Jansen ........................ 570/171 |
| 5,523,501 A | 6/1996 | Kellner et al. |
| 5,562,861 A | 10/1996 | Nimitz et al. |
| 5,621,151 A | 4/1997 | Manogue |
| 5,621,152 A | 4/1997 | Jansen et al. |
| 5,659,093 A | 8/1997 | Takubo et al. |
| 5,679,875 A | 10/1997 | Aoyama et al. |
| 5,723,699 A | 3/1998 | Miller et al. |
| 5,730,894 A | 3/1998 | Minor |
| 5,902,911 A | 5/1999 | Rao et al. |
| 5,919,994 A | 7/1999 | Rao |
| 6,018,083 A | 1/2000 | Manogue et al. |
| 6,065,547 A | 5/2000 | Ellis et al. |
| 6,156,944 A | 12/2000 | Pham et al. |
| 6,207,865 B1 | 3/2001 | Breitscheidel et al. ...... 568/705 |
| 6,211,135 B1 | 4/2001 | Miller et al. |
| 6,281,395 B1 | 8/2001 | Nappa et al. |
| 6,291,729 B1 | 9/2001 | Rao |
| 6,346,203 B1 | 2/2002 | Robin et al. |
| 6,376,727 B1 * | 4/2002 | Rao et al. ................... 570/157 |
| 6,461,530 B2 | 10/2002 | Robin et al. |
| 6,478,979 B1 | 11/2002 | Rivers et al. |
| 6,763,894 B2 | 7/2004 | Schoenrock et al. |
| 6,849,194 B2 | 2/2005 | Robin et al. |

FOREIGN PATENT DOCUMENTS

| | | |
|---|---|---|
| CA | 1162511 | 5/1991 |
| CA | 2081813 | 10/1992 |
| DE | 1546505 | 9/1970 |
| DE | 42 03 351 A1 | 8/1993 |
| EP | 0 039 471 A1 | 11/1981 |
| EP | 0 349 115 A1 | 1/1990 |
| EP | 0 383 443 A2 | 8/1990 |
| EP | 0 434 407 A1 | 6/1991 |
| EP | 0 434 409 A | 6/1991 |
| EP | 0 481 618 A1 | 4/1992 |
| EP | 0 570 367 B1 | 1/1993 |
| EP | 0 539 989 A1 | 5/1993 |
| EP | 0 539 989 B1 | 6/1997 |
| EP | 0 253 410 A | 1/1998 |
| GB | 428361 | 9/1930 |
| GB | 428445 | 5/1935 |
| GB | 468447 | 8/1937 |
| GB | 698386 | 10/1953 |
| GB | 790335 | 2/1958 |
| GB | 902590 | 8/1962 |
| GB | 1077932 | 8/1967 |
| GB | 1132636 | 11/1968 |
| GB | 1359023 | 7/1974 |
| GB | 1578933 | 11/1980 |
| GB | 2 120 666 | 12/1983 |
| GB | 2370768 | 7/2002 |
| JP | SHO 48-19093 | 3/1973 |
| JP | 51034595 | 9/1974 |
| JP | SHO 50-50864 | 4/1975 |
| JP | SHO 52-25679 | 7/1977 |
| JP | 57-93070 A | 6/1982 |
| JP | HEI 1-115999 | 5/1989 |
| JP | HEI 4-96770 | 3/1992 |
| RU | 2068718 C1 | 8/1990 |
| WO | WO 91/02564 | 3/1991 |
| WO | WO 91/04766 | 4/1991 |
| WO | WO 91/05752 | 5/1991 |
| WO | WO 91/12853 | 9/1991 |
| WO | 0 442 075 B1 | 8/1993 |
| WO | WO 93/24586 | 12/1993 |
| WO | WO 96/17813 | 6/1996 |
| WO | WO 96/40834 | 12/1996 |
| WO | WO 98/37043 | 8/1998 |
| WO | WO 98/50327 | 11/1998 |
| WO | WO 99/26907 | 11/1998 |
| WO | WO 99/51553 | 10/1999 |
| WO | WO 99/51555 | 10/1999 |
| WO | WO 99/62851 | 12/1999 |
| WO | WO 02/40102 A2 | 5/2002 |
| WO | WO 02/40102 A3 | 5/2002 |
| WO | PCT/US02/30729 | 9/2002 |
| WO | WO 02/078788 A2 | 10/2002 |
| WO | WO 02/078790 A2 | 10/2002 |
| WO | WO 02/078790 A3 | 10/2002 |
| WO | WO 02/078799 A3 | 10/2002 |
| WO | WO 03/029173 A | 4/2003 |
| WO | PCT/US2004/023917 | 7/2004 |
| WO | US2004/011563 | 7/2004 |

OTHER PUBLICATIONS

Decision of the Technical Board of Appeal Regarding European Patent No. 0439579, Nov. 14, 2001.

Dmitrii D. Moldavskii, "Technology for the Preparation of Perfluoro-Organic Compounds," *Journal of Fluorine Chemistry*, Elsevier Science S.A. (Netherlands), vol. 94 (No. 2), p. 157-167, (Feb. 5, 1999).

National Fire Protection Association, Standard on "Clean Agent Fire Extinguishing Systems"(2001), pp. 2001-1 and 2001-14.

Final Report on Extinguishing Agents for the Period Sep. 1, 1947 to Jun. 30, 1950 Covering Research Conducted by *Purdue Research Foundation and the Department of Chemistry* Purdue University, Contract W-44-009-engr 507, Army Engineers Research and Development Laboratories, Fort Belvoir.

"Report of the Halons Technical Options Committee", *United Nations Environment Program, Montreal Protocol Assessment, Technology Review*, Jun. 1989, Draft for Peer Review.

Kauschka, Von Gunther, et al., "Calculation of Thermodynamic Substance Data and Reaction Balance with Poly- and Perhalogen Hydrocarbons", Oct. 1976, *Chemistry Section of the Humboldt University in Berlin* vol. 10, pp. 1-22 (translated).

Smart, B.E., "Fluorocarbons", 1983, *The Chemistry of Functional Groups* Supplement D, Chapter 14, pp. 603-655.

Sittig, Marshall, "Fluorinated Hydrocarbons and Polymers", *Chemical Process Monograph No. 22*, 1966, p. 13.

Reid, Robert C., "The Properties of Gases and Liquids", 1987, pp. 153-157.

Hynes, Robert G., et al., "Shock-Tube Study of the Pyrolysis of the Halon Replacement Molecule $CF_3CHFCF_3$", 1999, *J. Phys. Chem. A*, vol. 103, pp. 54-61.

Joint Assessment of Commodity Chemicals No. 24,*Pentafluoroethane (HFC 125)*, (ECETOC) May 1994, pp. 1420.

Malcolm, J.E., "Halogenated Extinguishing Agents", Part II Research at the Corps ofEngineers' Laboratories, 1951, *NFPA Quarterly*, pp. 119-131.

Nelson, Thomas P., "Findings of the Chlorofluorocarbon Chemical Substitutes International Commitee", Apr. 1988, *U.S. Environmental Protection Agency, Air and Energy Engineering Research laboratory*, EPA/600/9-88/009, pp. i-K6.

Smart, Bruce E., *Fluorinated Organic Molecules*, 1986, Molecular Structure and Energetics, vol. 3, pp. 141, 152.

Nimitz, et al., "Halocarbons as Halon-Replacements: Technology Review and Initiation," NewMexico Engineering Research Institute, University of New Mexico, Final Report, Mar. 1991, 141 pages.

"A Review of the Toxic and Asphyxiating Hazards of Clean Agent Replacements for Halon 1301," A Report by the *Halon Alternatives Group*, Feb. 1995, 22 pages.

Hart-Winchester, "A Burning Issue: What Products Will Replace Halon 1301?" *The Computer Operations Manager*, Mar./Apr. 1995, pp. 13-18.

"Fire Protection Handbook, 14th Ed.", Nat'l Fire Protection Assoc., Boston, 2001 Sec. 13, Chap. 4, pp. 13-20 to 13-26.

Kirk-Othmer, "Encyclopedia of Chemical Technology," *Catalysis*, 3rd ed., John Wiley & Sons (New York), p. 16-18.

Milos Hudlicky, *Chemistry of Organic Fluorine Compounds, A Laboratory Manual with Comprehensive Literature Coverage*, 2nd ed., Ellis Horwood (New York), p. 170-179, (Feb. 8, 1992).

Jiri George Drobny; "*Technology of Fouorophlymers*"; Basic Chemistry of Fluoropolymers, pp. 8-11, 78-79; CRC Press.

Kirk-Othmer, "Encyclopedia of Chemical Technology," *Hydrofluorocarbons*, John Wiley & Sons, © 2001, p. 714-729.

Practical Dictionary of Organic Chemistry, GAO, Hongbin, Higher Education Press, Jul. 1997, p. 155.

Herbert O. House, "Catalytic Hydrogenation and Dehydrogenation," *Modern Synthetic Reactions*, 2nd ed., The Benjamin/Cummings Publishings Company (Menlo Park, CA), p. 1/2, 1983.

Derwent Publications, Ltd., Abstract; SU715092, Feb. 15, 1980; 1 page.

J. Kvicala. et al., "Preparation of Perhalogenated Chlorofluoropropanes by Halogen Exchange in the Liquid and Vapour Phases and Their Isomer Analyses by 19F NMR Spectroscopy," *Journal of Fluorine Chemistry*, Elsevier Sequoia (Netherlands), p. 155-175, (Feb. 5, 1989).

F.J. Mettillc, et al., "Methods for the Introductions of Hydrogen Into Fluorinated Compounds," *Fluorine Chemistry Reviews*, 1st ed., vol. 1 (No. 2), p. 315-358, (Feb. 5, 1967).

Dr. Mark D. Cisneros. et al., "*An Integrated Approach to Achieve Low Environmental Impact in the Special Hazards Five Suppression Industry,*" Great Lakes Chemical Corporation (West Lafayette, Indiana), p. 1-8, no date available.

Viacheslav A. Petrov, et al., "Isomerization of Halopolyfluoroalkanes by the Action of Aluminum Chlorofluoride." *Journal of Fluorine Chemistry*, Elsevier Science S.A. (Netherlands), p. 125-130, (Feb. 5, 1998).

B.P. Aggarwal, et al., "Chlorination of Propane and Propylene and Pyrolysis of Perchloropropane," *Petroleum & Hydrocarbons*, vol. 3 (No. 2), p. 69-72, (Jul. 5, 1968).

Albert L. Henne, et al., "*Fluorinated Derivatives of Propane and Propylene,*" p. 496-497, (Mar. 5, 1946).

Kirk-Othmer, "Encyclopedia of Chemical Technology," *Catalysis*, 3rd ed., John Wiley & Sones (New York), p. 16-18.

* cited by examiner

SYSTEMS AND METHODS FOR PRODUCING FLUOROCARBONS

This application is a divisional of U.S. application Ser. No. 10/641,527 filed on Aug. 13, 2003, and which is incorporated herein by reference.

TECHNICAL FIELD

The present invention relates to the production of fluorocarbons. Aspects of the present invention relate to the production of saturated and unsaturated fluorocarbons.

BACKGROUND OF THE INVENTION

Hydrofluorocarbons and fluoromonomers such as 1,1,1,2,3,3,3-heptafluoropropane ($CF_3CHFCF_3$, HFC-227ea) and hexafluoropropene ($CF_3CF=CF_2$, FC-1216, HFP) are commercially desired.

HFP is widely employed as a monomer for the production of fluorine-containing polymers, for example, the thermoplastic FEP ("fluorinated-ethylene-propylene") resins, formed via the copolymerization of tetrafluoroethylene and hexafluoropropene (see for example, *Fluorine Chemistry: A Comprehensive Treatment*, M. Howe-Grant, ed., Wiley & Sons, New York, N.Y., 1995, page 404).

HFC-227ea has found use as a blowing agent (U.S. Pat. No. 5,314,926; U.S. Pat. No. 5,278,196), refrigerant (Chen, J., *Sci. Tech. Froid* (1994), (2 CFCS, the Day After), 133-145), and propellant for use in metered dose inhalers (Clark, R., *Aerosol. Sci. Technol.*, (1995) 22, 374-391). The compound has also found widespread use as a fire suppression agent, for example, the protection of telecommunication facilities where it is marketed under the tradename FM-200® (Great Lakes Chemical Corporation, Indianapolis, Ind.) (Robin, M. L., *Process Safety Progress*, Volume 19, No. 2 (Summer 2000), p. 107-111).

Numerous methods are disclosed in the prior art for the preparation of halogenated compounds. These methods vary widely, due in part to the different halogens and functional groups involved. The prior art demonstrates that known methods do not readily translate into predictable applications for other compounds.

Methods have been reported for the production of FC-1216. These processes include the thermal cracking of tetrafluoroethylene (TFE) at reduced pressure and temperatures of 700C to 800C as well as the pyrolysis of polytetrafluoroethylene under vacuum at elevated temperatures can yield HFP.

Methods have been reported for the production of HFC-227ea. The vapor phase reaction between HFP and HF over an active carbon catalyst can produce HFC-227ea (GB 902,590). HFC-227ea has also been produced via the treatment of 1,1,1,3,3,3-hexafluoropropane ($CF_3CH_2CF_3$, HFC-236fa) with elemental fluorine (U.S. Pat. No. 5,780,691) and via the treatment of 2-chloro-1,1,1,3,3,3-hexafluoropropane (CFC-217ba) with HF (WO 99/40053).

It is desired to develop new methods and systems for economically favorable production of HFP and HFC-227ea, and it would be desired for such methods and systems to have broad utility for the production of saturated and unsaturated fluorocarbons.

SUMMARY OF THE INVENTION

Systems for producing fluorocarbons are provided that include, in some aspects, a reactant stream comprising a saturated halogenated fluorocarbon, a reactor configured to bring the saturated halogenated fluorocarbon into reactive proximity with a catalyst that includes Cu and Pd, and a product stream comprising saturated and unsaturated fluorocarbons.

According to an aspect of the present invention, methods for preparing fluorinated compounds are described that include contacting a reactant mixture that includes a C-3 saturated halogenated fluorocarbon and hydrogen with a catalyst having Pd and one or both of Ni and Cu. Such forms a mixture that includes a C-3 saturated hydrofluorocarbon and a C-3 unsaturated fluorocarbon.

In an aspect of the present invention, methods are described for contacting $CF_3CCl_2CF_3$ with hydrogen in the presence of a catalyst to produce a mixture that includes one or more of $CF_3CH_2CF_3$, $CF_3CHClCF_3$, $CF_3CH=CF_2$, and $CF_3CCl=CF_2$.

Methods for preparing fluorinated compounds are also described that include contacting a reactant mixture comprising a C-3 saturated halogenated fluorocarbon and hydrogen with a catalyst having one or more of K, Zr, Na, Ni, Cu, W, Zn, Fe, Mn, Co, Ti, and Pd to form a mixture that includes a C-3 unsaturated fluorocarbon and at least about 35% C-3 saturated hydrofluorocarbon.

Aspects of the present invention also provide methods for producing fluorocarbons that include contacting a reactant mixture comprising $CF_3CClFCF_3$ and hydrogen with a catalyst system that includes about 9:1 Cu to Pd (weight ratio) and activated carbon.

Aspects of the present invention can also include contacting a reaction mixture comprising $CF_3CClFCF_3$ with a catalyst system that includes about 9:1 Cu to Pd (weight ratio) for about 9 to about 55 seconds at a pressure of about 1.0 kg/cm$^2$ to about 10 kg/cm$^2$ and at a temperature of about 220° C. to about 350° C. to form a mixture comprising $CF_3CHFCF_3$ and $CF_3CF=CF_2$.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In one embodiment of the present invention, methods and systems are described for producing a co-stream of two products. Aspects of the present invention will be described with reference to FIGS. 1 and 2.

Figure 1:
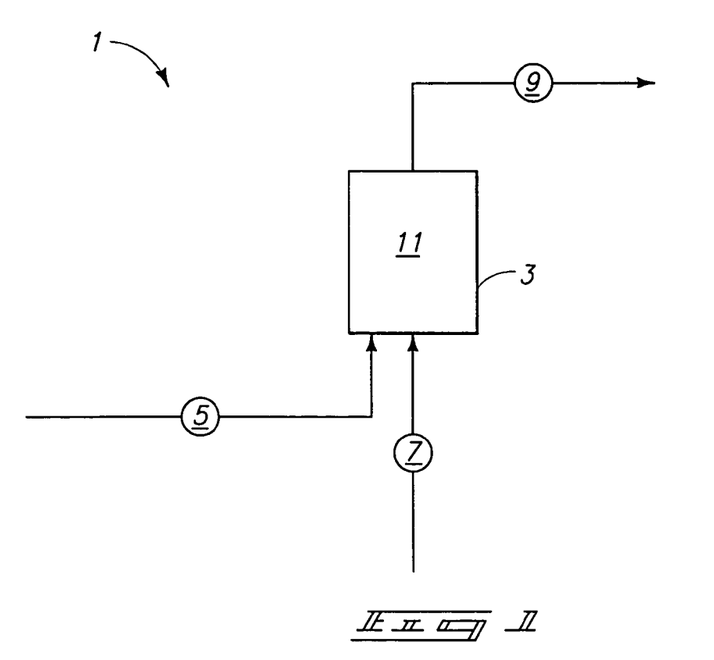
FIG. 1. is a diagram of an exemplary system for fluorocarbon production in accordance with an aspect of the present invention.

FIG. 1 depicts a fluorination reaction system 1 that includes a reactor 3, saturated halogenated fluorocarbon reactant 5, hydrogenation reactant 7, and product 9. Examples of saturated halogenated fluorocarbon 5 that can be utilized in accordance with the present invention include those saturated halogenated fluorocarbons that are fully halogenated, as well as, those that are less than fully halogenated. According to an aspect of the present invention, saturated halogenated fluorocarbon 5 includes C-3 saturated halogenated fluorocarbons. Examples of saturated halogenated fluorocarbon include $CF_3CClFCF_3$ (CFC-217ba) and/or $CF_3CCl_2CF_3$ (CFC-216aa).

Hydrogenation reactant 7 can include hydrogen. An exemplary hydrogenation reactant 7 includes diatomic hydrogen.

Generally, saturated halogenated fluorocarbon reactant 5 and hydrogenation reactant 7 can together form all or part of a reactant mixture and/or a reactant stream. As depicted in FIG. 1, saturated halogenated fluorocarbon reactant 5 and hydrogenation reactant 7 are provided to reactor 3 via independent streams. The present invention should not be so limited. Saturated halogenated fluorocarbon reactant 5 and hydrogenation reactant 7 may be combined prior to being transferred to reactor 3 or may be provided to reactor 3 via separate streams as illustrated.

Saturated halogenated fluorocarbon 5 may also be combined with hydrogenation reactant 7 at particular mole ratios. An aspect of the present invention provides combining hydrogenation reactant 7 and saturated halogenated fluorocarbon 5 at a mole ratio of hydrogenation reactant 7 to saturated halogenated fluorocarbon 5 from about 1:1 to about 20:1. Exemplary mole ratios of hydrogenation reactant 7 to saturated halogenated fluorocarbon 5 also include about 2.5:1 to about 20:1, about 1:1 to about 15:1, about 2:1 to about 10:1, and/or about 1:1 to about 5:1.

Figure 2:
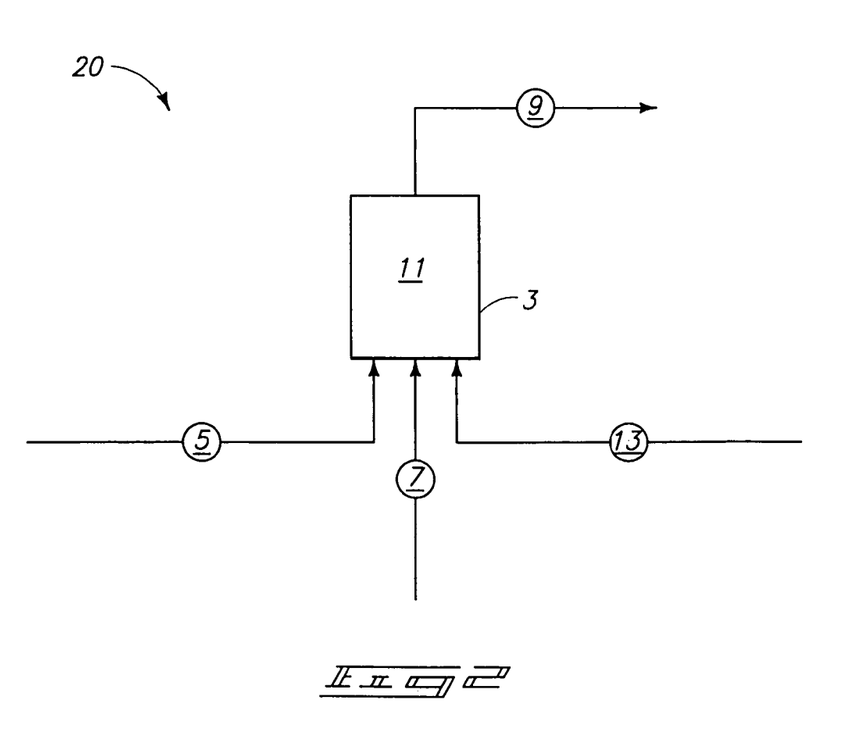
FIG. 2. is a diagram of an exemplary system for fluorocarbon production in accordance with another aspect of the present invention.

Aspects of the present invention also provide for the addition of a diluent. FIG. 2 illustrates a system 20 for preparing fluorocarbons according to the present invention that includes saturated halogenated fluorocarbon reactant 5, hydrogenation reactant 7, and diluent 13. Examples of diluent 13 that can be used in accordance with the present invention include hydrogen, helium, and argon gases, as well as, compounds such as $CF_3CFHCF_3$ (HFC-227ea) and $CF_3CH_2F$ (HFC-134a). Diluent 13 can be utilized in combination with hydrogenation reactant 7 and saturated halogenated fluorocarbon 5 at particular mole ratios. Examples of mole ratios useful in accordance with the present invention are diluent 13 to hydrogenation reactant 7 to saturated halogenated fluorocarbon reactant 5 ratios of from about 2:0.6:1 to about 15:5:1 and/or from about 3:1:1 to about 14:2.5:1.

Referring again to FIG. 1, the reactant mixture can be contacted with a catalyst 11 within a reactor 3. According to aspects of the present invention, reactor 3 is configured to bring the reactant mixture into reactive proximity with catalyst 11. Reactor 3 can include, but are not limited to, reactors such as those manufactured of Inconel® (INCO ALLOYS INTERNATIONAL, INC, Delaware) and configured to perform chemical reactions on a laboratory or industrial scale.

Catalyst 11 can comprise, consist essentially of, and/or consist of one or more catalyst precursors such as K, Zr, Na, Ni, W, Cu, Zn, Fe, Mn, Co, Ti, and Pd. In particular aspects, catalyst 11 comprises, consists essentially of, and/or consists of Pd and one or both of Ni and Cu. Catalyst 11 may include Cu and Pd at a weight ratio of Cu to Pd of from about 3:1 to about 28:1, about 8:1 to about 28:1, and/or a weight ratio of Cu to Pd of about 9:1. Catalyst 11 can be in pure or supported form. Examples of supports that can be utilized in accordance with the present invention include activated carbon, aluminum oxide, and/or silica gel supports. An exemplary activated carbon support includes Tekeda® activated carbon (Takeda Chemical Industries, Ltd., Higashi-ku, Osaka JAPAN).

Typically catalysts can be prepared according to accepted catalyst preparation techniques. Exemplary techniques include dissolving the selected catalyst precursor in a suitable solvent with or without support, removing solvent from the catalyst and/or support, and loading the reactor with the catalyst. Once in the reactor, the catalyst can be further prepared by heating the reactor and monitoring the evolution of solvent from the catalyst. The catalyst may be prepared and/or activated in the presence of gases such as hydrogen, helium, argon, and/or nitrogen.

The present invention also provides specific temperatures, pressures, and contact times within the reactor to facilitate the production of fluorocarbons. Systems and methods of the present invention also provide for contacting the reactant mixture with catalyst 11 within reactor 3 for specific amounts of time. This time is typically referred to as contact time and can be calculated from the flow rates of the reactants and the volume of the reactor containing catalyst. Exemplary contact times useful in accordance with the present invention can be from about 4 to about 75 seconds, from about 9 to about 55 seconds, from about 6 to about 30 seconds, and/or from about 10 to about 15 seconds.

In an exemplary aspect, the reaction temperature during contacting of catalyst 11 with the reaction mixture can be from about 100° C. to about 500° C., about 200° C. to about 400° C., about 220° C. to about 350° C. and/or about 220° C. to about 300° C.

Methods also provide for contacting the reactant mixture with catalyst 11 at pressures from about 1 $kg/cm^2$ to about 150 $kg/cm^2$, about 5 $kg/cm^2$ to about 10 $kg/cm^2$, or about 3 $kg/cm^2$ to about 8 $kg/cm^2$.

Referring to FIGS. 1 and 2, systems are depicted for producing a product mixture 9. Product mixture 9 can include saturated fluorocarbons such as hydrofluorocarbons and C-3 saturated hydrofluorocarbons. Exemplary components of product mixture 9 can include $CF_3CFHCF_3$ (HFC-227ea), $CF_3CH_2CF_3$ (HFC-236fa), and/or $CF_3CHClCF_3$ (CFC-226da). Product mixture 9 also includes an unsaturated fluorocarbon that can include C-3 unsaturated hydrofluorocarbons such as one or more of $CF_3CF=CF_2$ (HFP, FC-1215yc), $CF_3CH=CF_2$ (PFP, FC-1215zc), and/or $CF_3CCl=CF_2$ (CFC-1215xc). Exemplary aspects of the present invention include product mixtures that include $CF_3CHFCF_3$ (HFC-227ea) and $CF_3CF=CF_2$ (FC-1215yc). Other exemplary aspects of the present invention include product mixtures that include one or more of $CF_3CH_2CF_3$ (HFC-236fa), $CF_3CHClCF_3$ (CFC-226da), $CF_3CH=CF_2$ (FC-1215zc), and/or $CF_3CCl=CF_2$ (CFC-1215xc). Aspects of the present invention also provide product mixture 9 that can be at least about 35% saturated fluorocarbon.

Aspects of the present invention are further described with reference to the following non-limiting examples.

Catalyst Preparation

Catalysts utilized in the subsequent examples are prepared in accordance with the following methods.

Method A

The catalyst is prepared by weighing amounts of Takeda® activated carbon support and catalyst precursor into a beaker. Enough water, as a solvent, is added to cover the support and precursor and the mixture is stirred for approximately 15 minutes. The mixture is filtered under water aspirator pressure, and the catalyst is allowed to air dry. The catalyst is packed into the reactor and is heated at 150° C. under a $N_2$ stream until no water vapor is visibly apparent exiting the reactor. The heat is then increased to 200° C. until again no water vapor is visibly apparent exiting the reactor.

Method B

The catalyst is prepared by weighing amounts of Takeda® activated carbon support and catalyst precursor into a beaker. Enough $CH_2Cl_2$, as a solvent, is added to cover the support and precursor, and the mixture is stirred for approximately 15 minutes. The mixture is filtered under water aspirator pressure and the catalyst is allowed to air dry. The catalyst is packed into the reactor and is heated at 150° C. under a $N_2$ stream until no vapor is visibly apparent exiting the reactor. The heat is then increased to 200° C. until no vapor is visibly apparent exiting the reactor.

Method C

The catalyst is prepared by weighing amounts of Takeda® activated carbon support and catalyst precursor into a beaker. Enough water, as a solvent, is added to cover the support and precursor and the mixture is stirred for approximately 15 minutes. Sufficient NaOH is added to make the mixture alkaline (pH≧12). The mixture is then chilled in an ice bath to 10° C. $NaBH_4$ dissolved in NaOH is added drop-wise until reduction of the catalyst is achieved. The mixture is then heated to boiling until a dry catalyst remained. The catalyst mixture is then filtered and rinsed twice with water before being dried in vacuum oven for approximately 1.5 hours. The catalyst is then packed into a reactor and dried as in Method A.

Method D

The catalyst is prepared by weighing amounts of Takeda® activated carbon support and catalyst precursor into a beaker. Sufficient 5% (wt./wt.) HCl/water solution is added to the beaker to cover the support and precursor, and the mixture is heated to 100° C. for approximately 20 minutes. The mixture is then filtered, packed and dried as described in Method A.

Method E

The catalyst is prepared by weighing amounts of catalyst precursor into a beaker and covering with 5% (wt./wt.) HCl/water solution to form a mixture. The mixture is heated to 100° C. for approximately 20 minutes. To complete the catalyst, sufficient Takeda® activated carbon support to achieve the weight percent indicated is then added to the hot solution. The mixture is then hot filtered and dried as in Method A.

Method F

A catalyst of Cu, Pd, and support is prepared by weighing an amount of the catalyst precursor Cu into a beaker containing water. The solution is heated, and the percent Cu dissolved in the solution is then determined periodically until sufficient Cu is dissolved in the solution. Catalyst precursor Pd is weighed and placed in a beaker containing water. The solution is heated and the percent Pd dissolved in the solution is then determined periodically until sufficient Pd is dissolved in the solution. The Cu and Pd solutions are combined in a beaker to yield the desired ratios. Sufficient Takeda® activated carbon support is added and the solution stirred. The catalyst is air-dried and packed into the reactor and dried as described in Method A.

Method G

A catalyst of catalyst precursor is packed into the reactor. The reactor is heated to 350° C., and $H_2$ is passed over the catalyst at 126 cc/min for 16 hours.

Method H

A solution of 5% (wt./wt.) HCl and water is added to the catalyst precursor in a sufficient amount to wet the catalyst precursor. The wet catalyst is then dried under a $N_2$ stream overnight before being packed and dried as in Method A.

Method I

Catalyst is prepared as in Method E with the additional steps of reapplying the hot filtrate to the catalyst at least twice.

General Reaction Procedures

The reactor of examples 1-8 is a 36.20 cm long Inconel® tube with 1.27 cm outside diameter and a 33.0 cc volume. The reactor is mounted vertically in a Hoskins® (Hoskins Manufacturing Company Corporation. Hamburg, Mich.) electric furnace with a 30.5 cm heated zone controlled with a Watlow® (Watlow Electric Manufacturing Company, St. Louis, Mo.) series 956 temperature control unit. The reactor is equipped with internal and external thermocouples and a pressure gauge. Reactants are fed through calibrated Matheson® (Matheson Gas Products, Inc., Valley Forge, Pa.) flow meters and premixed before entering the heated zone.

Hydrogen is fed through a calibrated Hastings® (Teledyne Hastings Instruments, Teledyne Technologies, Inc., Los Angeles, Calif.) mass flow controller model HFC-202c with model 400 Hastings® power supply. CFC-217ba is fed with calibrated Eldex® (Eldex Laboratories, Inc., Napa, Calif.) metering pumps models A-60-S or B-100-S. The reactants are premixed and heated in a vaporizer before entering the reactor. Pressure is controlled with a proportional valve, driver module, and a Watlow® series 956 control unit. The exit gases are scrubbed through water, passed over Drierite® (W.A. Hammond Drierite Co., Xenia, Ohio), and analyzed by gas chromatography using a Hewlett-Packard® (Hewlett-Packard Company, Palo Alto, Calif.) 5890 series II gas chromatograph equipped with a 30 m×0.32 mm ID silicaplot™ (Varian, Inc., Palo Alto, Calif.) fused silica column and a flame ionization detector. Results are reported herein in area % of total area of response recorded by detector.

EXAMPLE 1

Potassium Catalysts

TABLE 1

| Catalyst Precursor | Cat. Prep. | Temp. (° C.) | Contact Time (sec) | $H_2$/CFC-217 Mole Ratio | % Conversion | % Selectivity HFP | HFC-227 | Total |
| --- | --- | --- | --- | --- | --- | --- | --- | --- |
| 10% KCl | A | 200 | 11.5 | 6.4 | 19.3 | 46.4 | 37.2 | 83.6 |
| 10% KCl | A | 250 | 18.7 | 3.9 | 45.6 | 52.0 | 19.8 | 71.9 |
| 10% KCl | A | 300 | 14.5 | 3 | 63.9 | 13.7 | 57.1 | 70.8 |

TABLE 2

| Catalyst Precursor | Cat. Prep. | Temp. (° C.) | Contact Time (sec) | $H_2$/CFC-217 Mole Ratio | % Conversion | % Selectivity HFP | HFC-227 | Total |
| --- | --- | --- | --- | --- | --- | --- | --- | --- |
| 10% KF | A | 300 | 10.6 | 4.1 | 6.9 | 6.2 | 65.9 | 72.1 |
| 10% KF | A | 250 | 9.7 | 4.4 | 7.22 | 8.1 | 66.6 | 74.7 |
| 10% KF | A | 300 | 9.6 | 7.1 | 14.0 | 49.3 | 27.5 | 76.8 |
| 10% KF | A | 350 | 3.4 | 5.2 | 59.6 | 29.5 | 31.7 | 61.1 |
| 10% KF | A | 400 | 7.9 | 5.6 | 38.7 | 24.7 | 20.4 | 55.0 |

EXAMPLE 2

Zirconium Catalysts

TABLE 3

| Catalyst Precursor | Cat. Prep. | Temp. (° C.) | Contact Time (sec) | $H_2$/CFC-217 Mole Ratio | % Conversion | % Selectivity HFP | HFC-227 | Total |
| --- | --- | --- | --- | --- | --- | --- | --- | --- |
| 10% $ZrCl_2$ | A | 200 | 11.5 | 4.1 | 25.31 | 38.0 | 56.1 | 94.1 |
| 10% $ZrCl_2$ | A | 250 | 10.3 | 8.2 | 66.18 | 46.1 | 36.1 | 82.3 |
| 10% $ZrCl_2$ | A | 300 | 9.5 | 6.8 | 36.43 | 38.9 | 36.6 | 75.5 |
| 10% $ZrCl_2$ | A | 350 | 8.8 | 7.3 | 93.63 | 18.7 | 47.4 | 66.1 |

TABLE 4

| Catalyst Precursor | Cat. Prep. | Temp. (° C.) | Contact Time (sec) | $H_2$/CFC-217 Mole Ratio | % Conversion | % Selectivity HFP | HFC-227 | Total |
| --- | --- | --- | --- | --- | --- | --- | --- | --- |
| 10% $ZrCl_4$ | B | 200 | 12.3 | 12.7 | 22.95 | 27.8 | 21.0 | 48.8 |
| 10% $ZrCl_4$ | B | 250 | 11.3 | 15.4 | 41.42 | 46.0 | 25.3 | 71.3 |
| 10% $ZrCl_4$ | B | 300 | 10.5 | 22.6 | 76.96 | 29.9 | 35.5 | 65.5 |
| 10% $ZrCl_4$ | B | 350 | 9.2 | 11.4 | 95.19 | 18.5 | 44.2 | 62.7 |

TABLE 5

| Catalyst Precursor | Cat. Prep. | Temp. (° C.) | Contact Time (sec) | $H_2$/CFC-217 Mole Ratio | % Conversion | % Selectivity HFP | HFC-227 | Total |
| --- | --- | --- | --- | --- | --- | --- | --- | --- |
| 10% $CuZrCl_2$ | B | 200 | 12.2 | 11.8 | 18.24 | 30.6 | 61.3 | 91.9 |
| 10% $CuZrCl_2$ | B | 250 | 11.1 | 11.6 | 40.41 | 59.8 | 28.7 | 88.5 |
| 10% $CuZrCl_2$ | B | 300 | 9.2 | 11.2 | 40.47 | 49.3 | 35.6 | 84.9 |
| 10% $CuZrCl_2$ | B | 350 | 9.4 | 13.3 | 37.6 | 46.6 | 36.9 | 83.5 |
| 10% $CuZrCl_2$ | B | 400 | 7.6 | 11.8 | 31.24 | 28.0 | 52.8 | 80.9 |
| 10% $CuZrCl_2$ | B | 500 | 7.6 | 14.7 | 31.84 | 4.0 | 32.0 | 36.1 |

EXAMPLE 3

Tungsten Catalysts

TABLE 6

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| 10% NaW | A | 200 | 12.1 | 10.3 | 23.1 | 44.5 | 40.3 | 84.7 |
| 10% NaW | A | 250 | 11 | 11.5 | 49.98 | 56.0 | 25.8 | 81.8 |
| 10% NaW | A | 300 | 10 | 10.1 | 95.19 | 40.2 | 27.0 | 87.2 |
| 10% NaW | A | 350 | 9.1 | 9.7 | 94.98 | 30.5 | 28.3 | 58.8 |

EXAMPLE 4

Support

TABLE 7

| Catalyst | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| Activated Carbon | A | 250 | 10.9 | 9.5 | 23.5 | 52.5 | 37.9 | 90.4 |
| Activated Carbon | A | 300 | 9.8 | 9 | 34.55 | 13.6 | 23.3 | 37.0 |
| Activated Carbon | A | 350 | 8.8 | 6.9 | 55.85 | 42.5 | 30.2 | 72.6 |
| Activated Carbon | A | 350 | 9.2 | 11 | 33.8 | 39.9 | 34.6 | 74.5 |

EXAMPLE 5

Nickel Catalysts

TABLE 8

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| NiF$_2$ | A | 200 | 12.2 | 11.8 | 45.8 | 57.0 | 8.0 | 65.0 |
| NiF$_2$ | A | 250 | 10.8 | 9.1 | 64.9 | 54.6 | 23.3 | 78.0 |
| NiF$_2$ | A | 250 | 17.1 | 4.2 | 30.1 | 67.9 | 18.8 | 76.8 |

TABLE 9

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| 10% NiCl$_2$ | C | 200 | 11.8 | 7.9 | 67.0-3 | 44.3 | 43.7 | 87.9 |
| 10% NiCl$_2$ | C | 250 | 10.7 | 8.4 | 49.55 | 60.5 | 23.8 | 84.3 |
| 10% NiCl$_2$ | C | 300 | 10 | 10.6 | 81.11 | 57.6 | 23.4 | 81.0 |
| 10% NiCl$_2$ | C | 350 | 9.1 | 9.4 | 73.81 | 65.8 | 6.5 | 72.3 |
| 10% NiCl$_2$ | C | 350 | 9.3 | 12 | 57.52 | 61.1 | 20.5 | 81.6 |

TABLE 10

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| 10% NiF$_2$ | D | 200 | 6.4 | 9.9 | 96.86 | 34.5 | 62.1 | 96.6 |
| 10% NiF$_2$ | D | 250 | 7.8 | 2.5 | 92.9 | 48.6 | 27.9 | 76.5 |
| 10% NiF$_2$ | D | 250 | 5.5 | 10.2 | 79.46 | 65.0 | 22.9 | 87.9 |

TABLE 11

| Catalyst Precursor | Cat. Prep. | Temp. (° C.) | Contact Time (sec) | $H_2$/CFC-217 Mole Ratio | % Conversion | % Selectivity HFP | HFC-227 | Total |
|---|---|---|---|---|---|---|---|---|
| 10% Ni(O) | A | 250 | 5.3 | 7.4 | 99.12 | 24.6 | 67.6 | 92.2 |
| 10% Ni(O) | A | 250 | 7.2 | 5.8 | 98.19 | 29.6 | 49.7 | 79.4 |
| 10% Ni(O) | A | 250 | 12.6 | 4.8 | 98.74 | 22.6 | 60.3 | 82.9 |

TABLE 12

| Catalyst Precursor | Cat. Prep. | Temp. (° C.) | Contact Time (sec) | $H_2$/CFC-217 Mole Ratio | % Conversion | % Selectivity HFP | HFC-227 | Total |
|---|---|---|---|---|---|---|---|---|
| 10% Nickel acetylacetonate | B | 200 | 11.7 | 7.4 | 60.73 | 51.9 | 38.9 | 90.8 |
| 10% Nickel acetylacetonate | B | 250 | 10.8 | 9.3 | 69.64 | 57.8 | 21.1 | 78.8 |
| 10% Nickel acetylacetonate | B | 300 | 10.1 | 5.5 | 97.33 | 55.1 | 20.3 | 75.4 |

TABLE 13

| Catalyst Precursor | Cat. Prep. | Temp. (° C.) | Contact Time (sec) | $H_2$/CFC-217 Mole Ratio | % Conversion | % Selectivity HFP | HFC-227ea | Total |
|---|---|---|---|---|---|---|---|---|
| 10% Bis(tripheylphosphine) nickel (11) bromide | B | 200 | 12 | 9.3 | 72.85 | 45.4 | 41.0 | 86.4 |
| 10% Bis(tripheylphosphine) nickel (11) bromide | B | 250 | 9.4 | 12.7 | 41.19 | 62.3 | 21.5 | 83.8 |
| 10% Bis(tripheylphosphine) nickel (11) bromide | B | 300 | 9.8 | 8.8 | 78.12 | 43.2 | 28.6 | 71.8 |

TABLE 14

| Catalyst Precursor | Cat. Prep. | Temp. (° C.) | Cont. Time (sec) | $H_2$/CFC-216 Mole Ratio | % Conv. | % Selectivity PFP | HFC-236fa | CFC-1215xc | CFC-226da |
|---|---|---|---|---|---|---|---|---|---|
| 10% $NiCl_2$ | C | 250 | 10.7 | 10.3 | 56.6 | 5.91 | nd | 22.3 | 60.6 |
| 10% $NiCl_2$ | C | 350 | 8.2 | 12.5 | 100 | 46.3 | 16.0 | nd | 2.6 |

EXAMPLE 6

Nickel/Palladium Catalysts

TABLE 15

| Catalyst Precursor | Cat. Prep. | Temp. (° C.) | Contact Time (sec) | $H_2$/CFC-217 Mole Ratio | % Conversion | % Selectivity HFP | HFC-227 | Total |
|---|---|---|---|---|---|---|---|---|
| $NiF_2$/Pd(O) (5% Ni/0.5% Pd) | A | 200 | 13.3 | 3.5 | 27.04 | 12.9 | 50.2 | 63.1 |
| $NiF_2$/Pd(O) (5% Ni/0.5% Pd) | A | 250 | 11 | 10.7 | 82.65 | 12.6 | 70.7 | 83.3 |
| $NiF_2$/Pd(O) (5% Ni/0.5% Pd) | A | 300 | 8.9 | 8.9 | 81.99 | 2.1 | 79.9 | 82.0 |

TABLE 16

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| NiF$_2$/PdCl2 (1.12% Ni/0.24% Pd) | A | 200 | 11.6 | 7.1 | 87.3 | 1.0 | 82.8 | 83.8 |
| NiF$_2$/PdCl2 (1.12% Ni/0.24% Pd) | A | 250 | 10.8 | 9.4 | 72.48 | 7.1 | 74.3 | 81.4 |
| NiF$_2$/PdCl2 (1.12% Ni/0.24% Pd) | A | 350 | 7.6 | 8.4 | 97.22 | 54.8 | 33.8 | 88.5 |
| NiF$_2$/PdCl2 (1.12% Ni/0.24% Pd) | A | 350 | 9.1 | 9.6 | 76.1 | 43.1 | 41.2 | 84.4 |

EXAMPLE 7

Copper Catalyst

TABLE 17

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| 10% CuCl | A | 200 | 11 | 5.0 | 34.27 | 40.0 | 55.7 | 95.6 |
| 10% CuCl | A | 250 | 8.3 | 2.2 | 39.63 | 57.3 | 37.2 | 94.5 |

TABLE 18

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| 10% CuF$_2$ | D | 200 | 6.6 | 9.3 | 26.34 | 41.8 | 43.1 | 84.9 |
| 10% CuF$_2$ | D | 250 | 5.8 | 6.6 | 56.18 | 14.0 | 77.8 | 91.8 |
| 10% CuF$_2$ | D | 300 | 5.3 | 7 | 90.72 | 47.5 | 46.6 | 94.1 |
| 10% CuF$_2$ | D | 300 | 5 | 7.5 | 31.48 | 71.8 | 24.6 | 96.4 |
| 10% CuF$_2$ | D | 300 | 5.1 | 8.5 | 58.09 | 60.5 | 36.4 | 96.9 |

EXAMPLE 8

Copper/Palladium Catalysts

TABLE 19

| Catalyst Precursor | Cat. Prep. | Temp. (° C.) | Contact Time (sec) | H$_2$/CFC-217 Mole Ratio | % Conversion | % Selectivity HFP | HFC-227 | Total |
|---|---|---|---|---|---|---|---|---|
| CuF$_2$/PdCl$_2$(5.51% Cu/0.42% Pd) | A | 250 | 10.2 | 12.8 | 49.86 | 28.9 | 69.4 | 98.3 |
| CuF$_2$/PdCl$_2$(5.51% Cu/0.42% Pd) | A | 250 | 10.2 | 12.8 | 94.98 | 30.2 | 68.6 | 98.8 |
| CuF$_2$/PdCl$_2$(5.51% Cu/0.42% Pd) | A | 250 | 14 | 13/4 | 97.3 | 33.0 | 66.0 | 99.0 |
| CuF$_2$/PdCl$_2$(5.51% Cu/0.42% Pd) | A | 250 | 12.9 | 6.2 | 69.05 | 29.5 | 69.2 | 98.6 |
| CuF$_2$/PdCl$_2$(5.51% Cu/0.42% Pd) | A | 300 | 11.1 | 4.4 | 94.94 | 33.2 | 64.9 | 98.1 |
| CuF$_2$/PdCl$_2$(5.51% Cu/0.42% Pd) | A | 300 | 8.2 | 5.4 | 92.8 | 38.7 | 59.8 | 98.5 |

TABLE 20

| Catalyst Precursor | Cat. Prep. | Temp. (° C.) | Contact Time (sec) | $H_2$/CFC-217 Mole Ratio | % Conversion | % Selectivity | | |
|---|---|---|---|---|---|---|---|---|
| | | | | | | HFP | HFC-227 | Total |
| $CuF_2/PdCl_2$(11.01% Cu/0.65% Pd) | A | 200 | 10.4 | 7.4 | 42.1 | 35.6 | 62.0 | 97.6 |
| $CuF_2/PdCl_2$(11.01% Cu/0.65% Pd) | A | 250 | 10.9 | 6.8 | 96.23 | 38.9 | 59.2 | 98.2 |
| $CuF_2/PdCl_2$(11.01% Cu/0.65% Pd) | A | 250 | 9.5 | 8.6 | 98.37 | 37.0 | 61.8 | 98.8 |

TABLE 21

| Catalyst Precursor | Cat. Prep. | Temp. (° C.) | Contact Time (sec) | $H_2$/CFC-217 Mole Ratio | % Conversion | % Selectivity | | |
|---|---|---|---|---|---|---|---|---|
| | | | | | | HFP | HFC-227 | Total |
| $CuF_2/PdCl_2$(5.51% Cu/0.65% Pd) | A | 200 | 11.8 | 8 | 73.36 | 22.4 | 72.1 | 94.6 |
| $CuF_2/PdCl_2$(5.51% Cu/0.65% Pd) | A | 250 | 11.8 | 8 | 97.79 | 35.0 | 63.7 | 98.6 |
| $CuF_2/PdCl_2$(5.51% Cu/0.65% Pd) | A | 250 | 12 | 9.4 | 97.3 | 40.61 | 58.03 | 98.6 |
| $CuF_2/PdCl_2$(5.51% Cu/0.65% Pd) | A | 250 | 12 | 9.2 | 98.23 | 41.4 | 57.5 | 98.9 |

TABLE 22

| Catalyst Precursor | Cat. Prep. | Temp. (° C.) | Contact Time (sec) | $H_2$/CFC-217 Mole Ratio | % Conversion | % Selectivity | | |
|---|---|---|---|---|---|---|---|---|
| | | | | | | HFP | HFC-227ea | Total |
| $CuF_2/PdCl_2$(5.51% Cu/0.675% Pd) | D | 250 | 11.4 | 6 | 99.24 | 32.5 | 64.6 | 97.1 |
| $CuF_2/PdCl_2$(5.51% Cu/0.675% Pd) | D | 250 | 11.4 | 13.9 | 93.42 | 33.6 | 65.8 | 99.4 |
| $CuF_2/PdCl_2$(5.51% Cu/0.675% Pd) | D | 250 | 12.5 | 15.1 | 99.23 | 33.1 | 47.3 | 30.4 |
| $CuF_2/PdCl_2$(5.51% Cu/0.675% Pd) | D | 250 | 6.19 | 7.8 | 33.13 | 31.8 | 63.0 | 94.8 |

TABLE 23

| Catalyst Precursor | Cat. Prep. | Temp. (° C.) | Contact Time (sec) | $H_2$/CFC-217 Mole Ratio | % Conversion | % Selectivity | | |
|---|---|---|---|---|---|---|---|---|
| | | | | | | HFP | HFC-227 | Total |
| $CuCl_2/PdCl_2$(5.5% Cu/0.6% Pd) | H | 230 | 9.5 | 6 | 93.27 | 40.7 | 58.0 | 98.7 |
| $CuCl_2/PdCl_2$(5.5% Cu/0.6% Pd) | H | 230 | 9.5 | 6 | 90.04 | 43.9 | 55.0 | 98.8 |
| $CuCl_2/PdCl_2$(5.5% Cu/0.6% Pd) | H | 230 | 9.6 | 4.5 | 68.24 | 41.3 | 57.8 | 99.1 |

TABLE 24

| Catalyst Precursor | Cat. Prep. | Temp. (° C.) | Contact Time (sec) | $H_2$/CFC-217 Mole Ratio | % Conversion | % Selectivity | | |
|---|---|---|---|---|---|---|---|---|
| | | | | | | HFP | HFC-227 | Total |
| $CuCl_2/PdCl_2$(5.5% Cu/0.6% Pd) | F | 200 | 15.1 | 15.5 | 98.98 | 30.4 | 68.1 | 98.4 |
| $CuCl_2/PdCl_2$(5.5% Cu/0.6% Pd) | F | 250 | 15.1 | 15.5 | 30.63 | 30.63 | 68.0 | 98.6 |

TABLE 25

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| CuCl$_2$/PdCl$_2$(5.5% Cu/0.9% Pd) | F | 275 | 9.5 | 4.4 | 94.38 | 43.8 | 49.0 | 92.9 |
| CuCl$_2$/PdCl$_2$(5.5% Cu/0.9% Pd) | F | 275 | 9.9 | 5.7 | 95.46 | 50.8 | 42.6 | 93.4 |

TABLE 26

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| CuCl$_2$/PdCl$_2$(2.0% Cu/0.6% Pd) | A | 200 | 27.8 | 5.3 | 97.66 | 0.9 | 76.2 | 77.1 |
| CuCl$_2$/PdCl$_2$(2.0% Cu/0.6% Pd) | A | 150 | 27.8 | 5.3 | 71.06 | 1.3 | 75.1 | 76.4 |
| CuCl$_2$/PdCl$_2$(2.0% Cu/0.6% Pd) | A | 100 | 27.8 | 5.3 | 34.54 | 2.8 | 69.7 | 72.4 |
| CuCl$_2$/PdCl$_2$(2.0% Cu/0.6% Pd) | A | 250 | 27.8 | 5.3 | 83.37 | 8.4 | 75.4 | 83.8 |

TABLE 27

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| CuCl$_2$/PdCl$_2$(5.5% Cu/0.6% Pd) | C | 200 | 9 | 5.2 | 53.58 | 29.3 | 69.4 | 98.7 |
| CuCl$_2$/PdCl$_2$(5.5% Cu/0.6% Pd) | C | 250 | 9.3 | 6.2 | 39.48 | 45.9 | 52.9 | 98.8 |
| CuCl$_2$/PdCl$_2$(5.5% Cu/0.6% Pd) | C | 230 | 9.7 | 3.6 | 72.3 | 44.4 | 54.6 | 99.0 |
| CuCl$_2$/PdCl$_2$(5.5% Cu/0.6% Pd) | C | 230 | 16 | 4.7 | 75.81 | 46.8 | 52.2 | 99.0 |
| CuCl$_2$/PdCl$_2$(5.5% Cu/0.6% Pd) | C | 230 | 21.8 | 3 | 30.54 | 36.1 | 62.9 | 99.0 |
| CuCl$_2$/PdCl$_2$(5.5% Cu/0.6% Pd) | C | 230 | 35.4 | 1.2 | 88.17 | 26.71 | 71.21 | 97.9 |

TABLE 28

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| CuF$_2$/PdCl$_2$(12.5% Cu/1.4% Pd) | I | 250 | 8.9 | 6.8 | 91.67 | 35.4 | 63.5 | 98.9 |
| CuF$_2$/PdCl$_2$(12.5% Cu/1.4% Pd) | I | 275 | 9.9 | 6.7 | 98.56 | 43.0 | 55.7 | 98.8 |
| CuF$_2$/PdCl$_2$(12.5% Cu/1.4% Pd) | I | 300 | 5.1 | 9.5 | 97.46 | 50.7 | 48.2 | 98.9 |
| CuF$_2$/PdCl$_2$(12.5% Cu/1.4% Pd) | I | 350 | 5 | 6.4 | 99.53 | 51.0 | 45.7 | 96.7 |
| CuF$_2$/PdCl$_2$(12.5% Cu/1.4% Pd) | I | 350 | 4 | 5.7 | 98.59 | 53.6 | 43.4 | 97.0 |
| CuF$_2$/PdCl$_2$(12.5% Cu/1.4% Pd) | I | 350 | 3 | 5.8 | 95.34 | 54.0 | 44.3 | 98.2 |
| CuF$_2$/PdCl$_2$(12.5% Cu/1.4% Pd) | I | 350 | 2 | 5.8 | 86.29 | 52.6 | 45.6 | 98.2 |

TABLE 29

| Catalyst Precursor | Cat. Prep. | Temp (° C.) | Cont. Time (sec) | H$_2$/CFC-216 Mole Ratio | % Conv. | % Selectivity | | | |
|---|---|---|---|---|---|---|---|---|---|
| | | | | | | PFP | HFC-236fa | CFC-1215xc | CFC-226da |
| CuCl$_2$/PdCl$_2$(5.5% Cu/0.2% Pd) | C | 100 | 11 | 11.8 | 99.9 | 38.6 | 28.6 | 28.6 | nd |
| CuCl$_2$/PdCl$_2$(5.5% Cu/0.2% Pd) | C | 125 | 8.6 | 8.1 | 91.6 | 26.0 | 16.4 | 19.2 | 34.9 |
| CuCl$_2$/PdCl$_2$(5.5% Cu/0.2% Pd) | C | 150 | 11.8 | 8.1 | 97.0 | 46.5 | 11.2 | 18.6 | 21.3 |
| CuCl$_2$/PdCl$_2$(5.5% Cu/0.2% Pd) | C | 175 | 11.8 | 8.1 | 98.5 | 58.2 | 6.7 | 20.3 | 12.8 |
| CuCl$_2$/PdCl$_2$(5.5% Cu/0.2% Pd) | C | 200 | 8.6 | 13 | 100 | 58.3 | 7.3 | 19.0 | 8.5 |
| CuCl$_2$/PdCl$_2$(5.5% Cu/0.2% Pd) | C | 270 | 6.8 | 12.2 | 100 | 27.7 | 12.4 | 36.4 | 20.2 |
| CuCl$_2$/PdCl$_2$(5.5% Cu/0.2% Pd) | C | 380 | 14.4 | 7.7 | 100 | 84.8 | 8.8 | 1.7 | nd |
| CuCl$_2$/PdCl$_2$(5.5% Cu/0.2% Pd) | C | 380 | 14.4 | 7.7 | 100 | 84.4 | 8.5 | 2.5 | nd |
| CuCl$_2$/PdCl$_2$(5.5% Cu/0.2% Pd) | C | 400 | 7.5 | 10.4 | 100 | 60.0 | 3.2 | 28.3 | nd |
| CuCl$_2$/PdCl$_2$(5.5% Cu/0.2% Pd) | C | 500 | 7.5 | 10.4 | 100 | 67.9 | 2.3 | 11.2 | nd |

EXAMPLE 9

Zinc Catalysts

TABLE 30

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| 20% ZnCl$_2$ | A | 300 | 12.8 | 6.4 | 100 | 46.46 | 46.46 | 92.92 |
| 20% ZnCl$_2$ | A | 300 | 12.46 | 5.33 | 99.39 | 42.58 | 50.26 | 92.84 |
| 20% ZnCl$_2$ | A | 300 | 12.33 | 4.57 | 74.38 | 39.54 | 51.64 | 91.18 |
| 20% ZnCl$_2$ | A | 450 | 18.54 | 4 | 84.06 | 48.26 | 40.63 | 88.89 |
| 20% ZnCl$_2$ | A | 450 | 14.37 | 5.5 | 83.83 | 24.11 | 55.02 | 79.13 |

EXAMPLE 10

Iron Catalysts

TABLE 31

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| 10% FeCl$_3$ | A | 500 | 5.87 | 3.62 | 81.06 | 41.65 | 45.11 | 86.76 |
| 10% FeCl$_3$ | A | 500 | 8.57 | 4.12 | 73.28 | 20.51 | 61.16 | 81.67 |
| 10% FeCl$_3$ | A | 500 | 7.67 | 10.5 | 93.39 | 40.44 | 42.23 | 82.67 |

EXAMPLE 11

Manganese Catalysts

TABLE 32

| Catalyst Precursor | Cat. Prep. | Temp. (° C.) | Contact Time (sec) | H$_2$/CFC-217 Mole Ratio | % Conversion | % Selectivity | | |
|---|---|---|---|---|---|---|---|---|
| | | | | | | HFP | HFC-227 | Total |
| 19% MnCl$_2$ | A | 400 | 24.69 | 4.33 | 63.6 | 10.22 | 59.42 | 69.64 |
| 19% MnCl$_2$ | A | 450 | 22.21 | 3 | 24.99 | 5.16 | 62.1 | 67.26 |
| 19% MnCl$_2$ | A | 500 | 16.24 | 9.5 | 60.29 | 6.63 | 62.26 | 68.89 |

EXAMPLE 12

Cobalt Catalysts

TABLE 33

| Catalyst Precursor | Cat. Prep. | Temp. (° C.) | Contact Time (sec) | $H_2$/CFC-217 Mole Ratio | % Conversion | % Selectivity HFP | HFC-227 | Total |
|---|---|---|---|---|---|---|---|---|
| 20% $CoCl_2$ | A | 400 | 24.14 | 4.33 | 36.26 | 9.16 | 63.38 | 72.54 |
| 20% $CoCl_2$ | A | 500 | 16.69 | 9.5 | 99.05 | 38.99 | 34 | 72.99 |
| 20% $CoCl_2$ | A | 500 | 16.59 | 9.5 | 99.66 | 29.22 | 33.23 | 62.45 |
| 20% $CoCl_2$ | A | 500 | 14.36 | 3.8 | 69.14 | 10.67 | 69.51 | 80.18 |

EXAMPLE 13

Titanium Catalysts

TABLE 34

| Catalyst Precursor | Cat. Prep. | Temp (° C.) | Contact Time (sec) | $H_2$/CFC-217 Mole Ratio | % Conversion | % Selectivity HFP | HFC-227 | Total |
|---|---|---|---|---|---|---|---|---|
| 20% bis(cyclopentadienyl) titanium dichloride | B | 200 | 12.12 | 4.22 | 2.66 | 17.67 | 6.39 | 24.06 |
| 20% bis(cyclopentadienyl) titanium dichloride | B | 300 | 12.34 | 4.57 | 12.54 | 38.52 | 38.52 | 77.04 |
| 20% bis(cyclopentadienyl) titanium dichloride | B | 400 | 24.25 | 4.33 | 42.72 | 17.09 | 38.95 | 56.04 |
| 20% bis(cyclopentadienyl) titanium dichloride | B | 450 | 21.71 | 2.4 | 30.28 | 13.97 | 50.56 | 64.53 |
| 20% bis(cyclopentadienyl) titanium dichloride | B | 500 | 16.39 | 9.5 | 98.21 | 14.8 | 53.99 | 38.79 |
| 20% bis(cyclopentadienyl) titanium dichloride | B | 500 | 16.34 | 9.5 | 91.48 | 30.05 | 34.9 | 64.95 |

EXAMPLE 14

Reaction Pressure

TABLE 35

| Catalyst Precursor | Cat. Prep. | Temp. (C.) | Pressure (kg/cm$^2$) | Contact Time (sec) | $H_2$/217 Mole Ratio | Conv. % | % Selectivity HFP | HFC-227 | Total |
|---|---|---|---|---|---|---|---|---|---|
| $CuF_2$/$PdCl_2$(11.01% Cu/0.65% Pd) | I | 250 | 1 | 9.5 | 8.6 | 98.4 | 37.0 | 61.8 | 98.8 |
| $CuF_2$/$PdCl_2$(12.5% Cu/1.4% Pd) | I | 275 | 1 | 10.4 | 6.7 | 97.8 | 40.1 | 58.9 | 99.0 |
| $CuF_2$/$PdCl_2$(12.5% Cu/1.4% Pd) | I | 300 | 1 | 9.9 | 6.7 | 99.9 | 46.7 | 50.4 | 97.1 |
| $CuF_2$/$PdCl_2$(12.5% Cu/1.4% Pd) | I | 350 | 1 | 3 | 5.8 | 95.3 | 54.0 | 44.3 | 98.2 |
| $CuF_2$/$PdCl_2$(5.5% Cu/0.9% Pd) | I | 250 | 1 | 8.9 | 5.3 | 91.3 | 36.2 | 59.7 | 95.9 |
| $CuF_2$/$PdCl_2$(5.5% Cu/0.9% Pd) | I | 300 | 1 | 9.1 | 4.2 | 91.5 | 50.0 | 44.9 | 94.9 |
| $CuF_2$/$PdCl_2$(5.5% Cu/0.9% Pd) | I | 300 | 8 | 9.8 | 7.2 | 74.5 | 21.8 | 75.0 | 96.8 |
| $CuF_2$/$PdCl_2$(5% Cu/0.6% Pd) | I | 350 | 8 | 3.8 | 4.9 | 42.6 | 28.0 | 70.5 | 98.4 |

EXAMPLE 15

With Diluent

TABLE 36

| Catalyst Precursor | Cat. Prep. | Temp. (C.) | Pressure (kg/cm$^2$) | Contact Time (sec) | Diluent | Diluent:H$_2$:217 Mole Ratio | Conv. % | % Selectivity HFP | 227 | Total |
|---|---|---|---|---|---|---|---|---|---|---|
| CuCl$_2$/PdCl$_2$(5% Cu/0.6% Pd) | C | 350 | 8.9 | 5.1 | He | 6:1:1.1:1 | 59.3 | 32.8 | 63.7 | 96.5 |
| CuCl$_2$/PdCl$_2$(5% Cu/0.6% Pd) | C | 350 | 6.1 | 16.7 | He | 2.3:0.38:1 | 56.7 | 26.4 | 68.5 | 94.9 |
| CuCl$_2$/PdCl$_2$(5% Cu/0.6% Pd) | C | 350 | 6.1 | 13.1 | HFC-134 | 9.8:1.9:1 | 90.8 | 35.7 | 62.3 | 98 |
| CuCl$_2$/PdCl$_2$(5% Cu/0.6% Pd) | C | 350 | 6.4 | 10.8 | HFC-227ea | 14:2.5:1 | 99.3 | 19.2 | 78.5 | 97.7 |
| CuCl$_2$/PdCl$_2$(5% Cu/0.6% Pd) | C | 350 | 1 | 9.8 | HFC-227ea | 5.3:0.4:1 | 67.2 | 40.7 | 58.4 | 99.1 |
| CuCl$_2$/PdCl$_2$(5% Cu/0.6% Pd) | C | 350 | 1 | 9.3 | HFC-227ea | 4.4:1.9:1 | 50.8 | 42.9 | 55.7 | 98.5 |

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A system for producing fluorocarbons comprising:
   a reactant stream comprising hydrogen and one or both of $CF_3CCl_2CF_3$ and $CF_3CClFCF_3$;
   a reactor configured to bring the saturated halogenated fluorocarbon into reactive proximity with a catalyst, wherein the catalyst consists essentially of Cu and Pd, a weight ratio of Cu to Pd being from about 3:1 to about 28:1; and
   a product stream comprising:
   one or more of $CF_3CF=CF_2$, $CF_3CH=CF_2$, and $CF_3CCl=CF_2$; and
   one or more of $CF_3CFHCF_3$, $CF_3CH_2CF_3$, and $CF_3CHClCF_3$.

2. The system of claim 1 wherein the weight ratio of Cu to Pd is about 9:1.

3. The system of claim 1 wherein the reactant stream consists essentially of $CF_3CClFCF_3$.

4. The system of claim 1 wherein the reactant stream consists essentially of $CF_3CCl_2CF_3$.

5. The system of claim 1 wherein the product stream consists essentially of:
   one or both of $CF_3CFHCF_3$ and $CF_3CH_2CF_3$; and
   one or both of $CF_3CF=CF_2$ and $CF_3CH=CF_2$.

6. The system of claim 1 wherein the product stream consists essentially of $CF_3CFHCF_3$ and $CF_3CF=CF_2$.

7. The system of claim 1 wherein the product stream comprises at least about 35% (wt./wt.) of the one or more of $CF_3CFHCF_3$, $CF_3CH_2CF_3$, and $CF_3CHClCF_3$.

8. The system of claim 1 wherein the catalyst further consists essentially of an activated carbon support.

9. The system of claim 1 wherein a pressure within the reactor is maintained at from about 3 kg/cm$^2$ to about 8 kg/cm$^2$.

10. The system of claim 1 wherein a temperature within the reactor is maintained at from about 220° C. to about 350° C.

* * * * *